(12) United States Patent
Hersman

(10) Patent No.: US 7,281,393 B2
(45) Date of Patent: Oct. 16, 2007

(54) METHOD AND APPARATUS FOR ACCUMULATING HYPERPOLARIZED XENON

(75) Inventor: F. William Hersman, Durham, NH (US)

(73) Assignee: University of New Hampshire, Durham, NH (US)

( * ) Notice: Subject to any disclaimer, the term of this patent is extended or adjusted under 35 U.S.C. 154(b) by 9 days.

(21) Appl. No.: 11/111,442

(22) Filed: Apr. 21, 2005

(65) Prior Publication Data

US 2005/0235693 A1  Oct. 27, 2005

Related U.S. Application Data

(60) Provisional application No. 60/564,076, filed on Apr. 21, 2004.

(51) Int. Cl.
*F25J 1/00*  (2006.01)
(52) U.S. Cl. ..................................................... 62/601
(58) Field of Classification Search ................. 62/601, 62/55.5
See application file for complete search history.

(56) References Cited

U.S. PATENT DOCUMENTS

| | | | |
|---|---|---|---|
| 3,024,009 A * | 3/1962 | Booth, Jr. et al. ............ | 62/55.5 |
| 3,378,351 A * | 4/1968 | Hashman et al. ............. | 62/601 |
| 3,904,272 A | 9/1975 | Straka | |
| 4,386,950 A * | 6/1983 | Bell et al. ..................... | 62/601 |
| 4,755,201 A * | 7/1988 | Eschwey et al. ............. | 62/637 |
| 4,793,357 A | 12/1988 | Lindstrom | |
| 4,977,749 A * | 12/1990 | Sercel ........................ | 62/51.1 |
| 5,545,396 A | 8/1996 | Albert et al. | |
| 5,617,859 A | 4/1997 | Souza et al. | |
| 5,642,625 A | 7/1997 | Cates, Jr. et al. | |
| 5,860,295 A * | 1/1999 | Cates et al. ................... | 62/637 |
| 6,305,190 B1 * | 10/2001 | Driehuys et al. ............. | 62/637 |
| 6,427,452 B2 * | 8/2002 | Zollinger et al. ............ | 62/51.1 |
| 6,434,284 B1 | 8/2002 | Savchenko | |

* cited by examiner

*Primary Examiner*—William C Doerrler
(74) *Attorney, Agent, or Firm*—Devine, Millimet & Branch; Paul C. Remus; Raymond I. Bruttomesso, Jr.

(57) ABSTRACT

A method and apparatus for the accumulation of hyperpolarized $^{129}$Xe is described. A gas mixture comprising $^{129}$Xe is flowed through a heat exchanger tube from the first end to the second end. Concurrently, the outer surface of the heat exchanger tube is controllably refrigerated, beginning with the second end, to a temperature low enough to freeze the $^{129}$Xe on the inner surface of the heat exchanger tube.

10 Claims, 4 Drawing Sheets

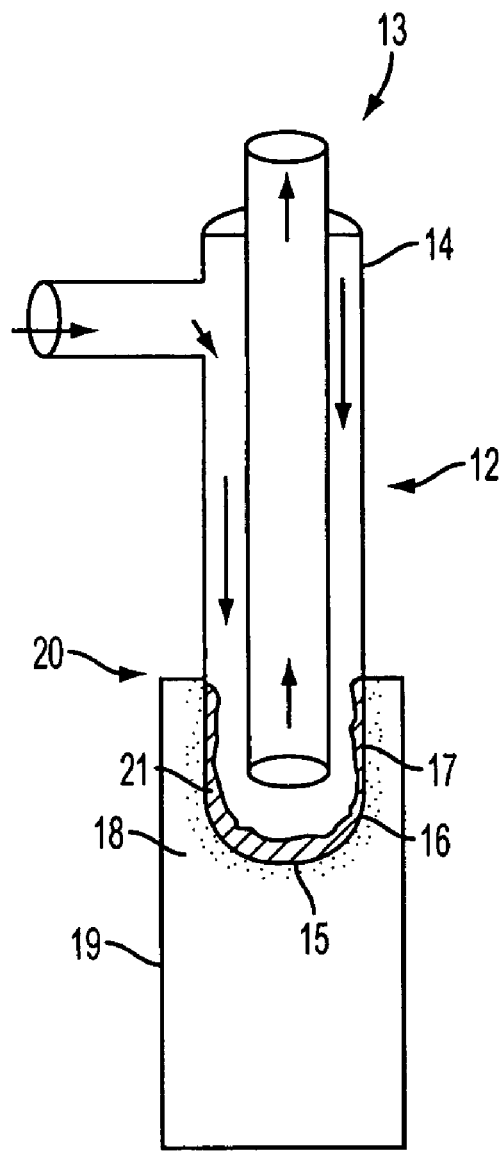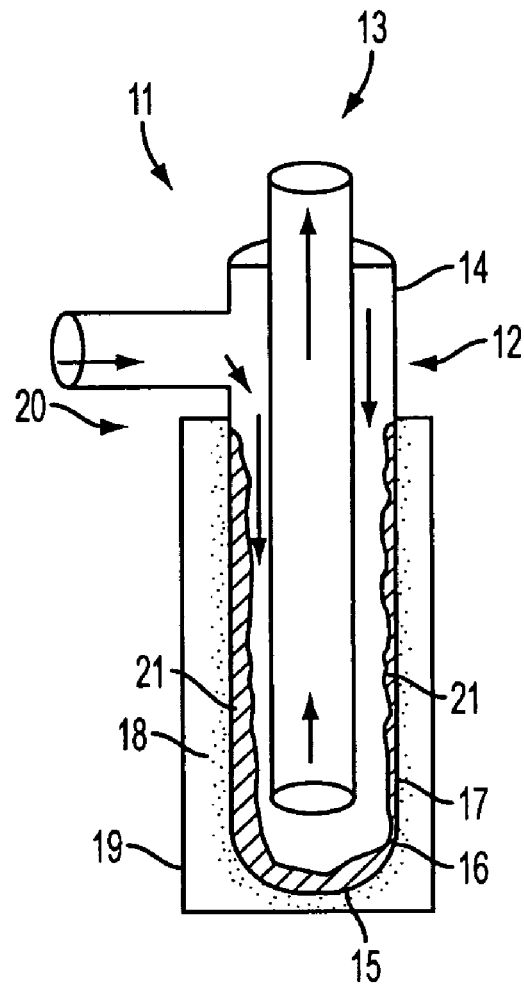
FIG. 2A
FIG. 2B

METHOD AND APPARATUS FOR ACCUMULATING HYPERPOLARIZED XENON

CROSS-REFERENCE TO RELATED APPLICATIONS

The present application claims the benefit of Provisional Application Ser. No. 60/564,076 filed Apr. 21, 2004, which is incorporated herein by reference.

FIELD OF THE INVENTION

The present invention relates to hyperpolarizing a noble gas. Specifically, the present invention relates to a method and apparatus for accumulating quantities of hyperpolarized xenon ($^{129}$Xe) in a continuous manner.

BACKGROUND INFORMATION

Hyperpolarized xenon ($^{129}$Xe) is becoming the contrast agent of choice in a broad spectrum of diagnostic protocols. Specifically, hyperpolarized $^{129}$Xe offers extraordinary potential as a contrast agent for magnetic resonance imaging ("MRI").

$^{129}$Xe is hyperpolarized by spin-exchange optical pumping using gas mixtures of Xe (with natural abundance of $^{129}$Xe or enriched in $^{129}$Xe), a quenching gas (nitrogen or hydrogen) and a buffer gas. $^{129}$Xe comprises only a fraction of the total gas mixture. One embodiment of this method is described in U.S. patent application Ser. No. 09/904,294.

The hyperpolarized $^{129}$Xe is then separated from the other gases in the gas mixture and accumulated by freezing at a temperature below the freezing point of $^{129}$Xe but above the freezing point of the other gases and in a high strength, e.g., 3,000 Gauss, magnetic field. The frozen hyperpolarized $^{129}$Xe has a longer polarization lifetime if it is then kept at temperatures closer to the temperature of liquid nitrogen rather than at temperatures close to its freezing point.

In the prior art, a preferred method of freezing the $^{129}$Xe uses a counter flow cold trap—cooled by liquid nitrogen or some other cryogen, as described in U.S. Pat. No. 5,809,801. The gas mixture is flowed down the insulated center cell of two concentric cells immersed in liquid nitrogen and up the outer cell. The frozen $^{129}$Xe is deposited at the bottom of the concentric cells where it first contacts the cold surface of the outer cell. As more $^{129}$Xe is flowed through the concentric cells, additional frozen $^{129}$Xe is deposited on the previously frozen $^{129}$Xe at the bottom of the concentric cells, thereby creating a lump of frozen $^{129}$Xe.

This method of accumulating hyperpolarized $^{129}$Xe has two significant drawbacks. First, the volume of $^{129}$Xe that can be accumulated is limited by the available volume at the bottom of the concentric cells. Second, the frozen $^{129}$Xe loses polarization faster if its temperature is just below its freezing point as compared to temperatures well below its freezing point. In order to freeze additional gaseous $^{129}$Xe through contact with the frozen $^{129}$Xe, heat must be transported through the frozen $^{129}$Xe, warming it, increasing the relaxation of the frozen $^{129}$Xe. In addition, the lump of frozen $^{129}$Xe cannot be thawed quickly and dwells near its freezing point when being thawed for use, again increasing the relaxation of the frozen $^{129}$Xe.

The present invention comprises a method and apparatus for separating and accumulating $^{129}$Xe that is not dependent on a limited volume in which to accumulate the frozen $^{129}$Xe. Moreover, the method and apparatus of the present invention does not freeze $^{129}$Xe by bringing gaseous $^{129}$Xe into contact with previously frozen $^{129}$Xe, thereby warming the frozen $^{129}$Xe. IT also provides for the more rapid thawing for use of the frozen $^{129}$Xe.

SUMMARY OF THE INVENTION

The present invention is a method and apparatus for accumulating hyperpolarized $^{129}$Xe. A gas mixture is flowed through a heat exchanger tube from a first end to a second end. Then beginning with the second end, the outer surface of the heat exchanger tube is controllably refrigerated to a temperature that is below the freezing point of $^{129}$Xe but above the freezing point of the other gases in the gas mixture.

Controllably refrigerating the outer surface of the heat exchanger tube, causes a thin layer of frozen $^{129}$Xe of uniform thickness to be deposited on the inner surface of the heat exchanger tube. The temperature of the thin layer of frozen $^{129}$Xe can be reduced to well below its freezing point more rapidly, and can be thawed for use more rapidly, than the methods of accumulating $^{129}$Xe described in the prior art, resulting in less relaxation of the frozen $^{129}$Xe.

BRIEF DESCRIPTION OF THE DRAWINGS

These and other features and advantages of the present invention will be better understood by reading the following detailed description, taken together with the drawings wherein:

FIG. 2A is a cross-sectional diagram of a preferred embodiment of the present invention in which a heat exchanger tube is partially immersed in a cryogen.

FIG. 2B is a cross-sectional diagram of a preferred embodiment of the present invention in which a heat exchanger tube is fully immersed in a cryogen.

DETAILED DESCRIPTION OF THE INVENTION

Optical pumping of an alkali vapor (usually rubidium) is used to polarize $^{129}$Xe nuclei. A sample of $^{129}$Xe, rubidium metal, and other gases (nitrogen, helium), is placed in a uniform magnetic field and warmed to achieve an optimal rubidium vapor density. A beam of photons at the resonant D1 absorption wavelength of the rubidium (794.7 nm) is circularly polarized and directed along the field to the sample. Absorption of photons excites the rubidium atom and flips the electron spin. De-excitation radiation is quenched by the nitrogen. As the rubidium becomes polarized, it also becomes increasingly transparent. Over time, the rubidium atomic polarization is transferred to the $^{129}$Xe nucleus, a process called spin-exchange.

The hyperpolarized $^{129}$Xe is then separated from the other gases in the sample by freezing the $^{129}$Xe at a temperature below the freezing point of $^{129}$Xe but above the freezing point of the other gases. Because $^{129}$Xe polarization relaxation is slower in frozen $^{129}$Xe, for example, the hyperpolarized $^{129}$Xe is then accumulated by freezing in a high strength magnetic field (over 500 Gauss).

Figure 1:
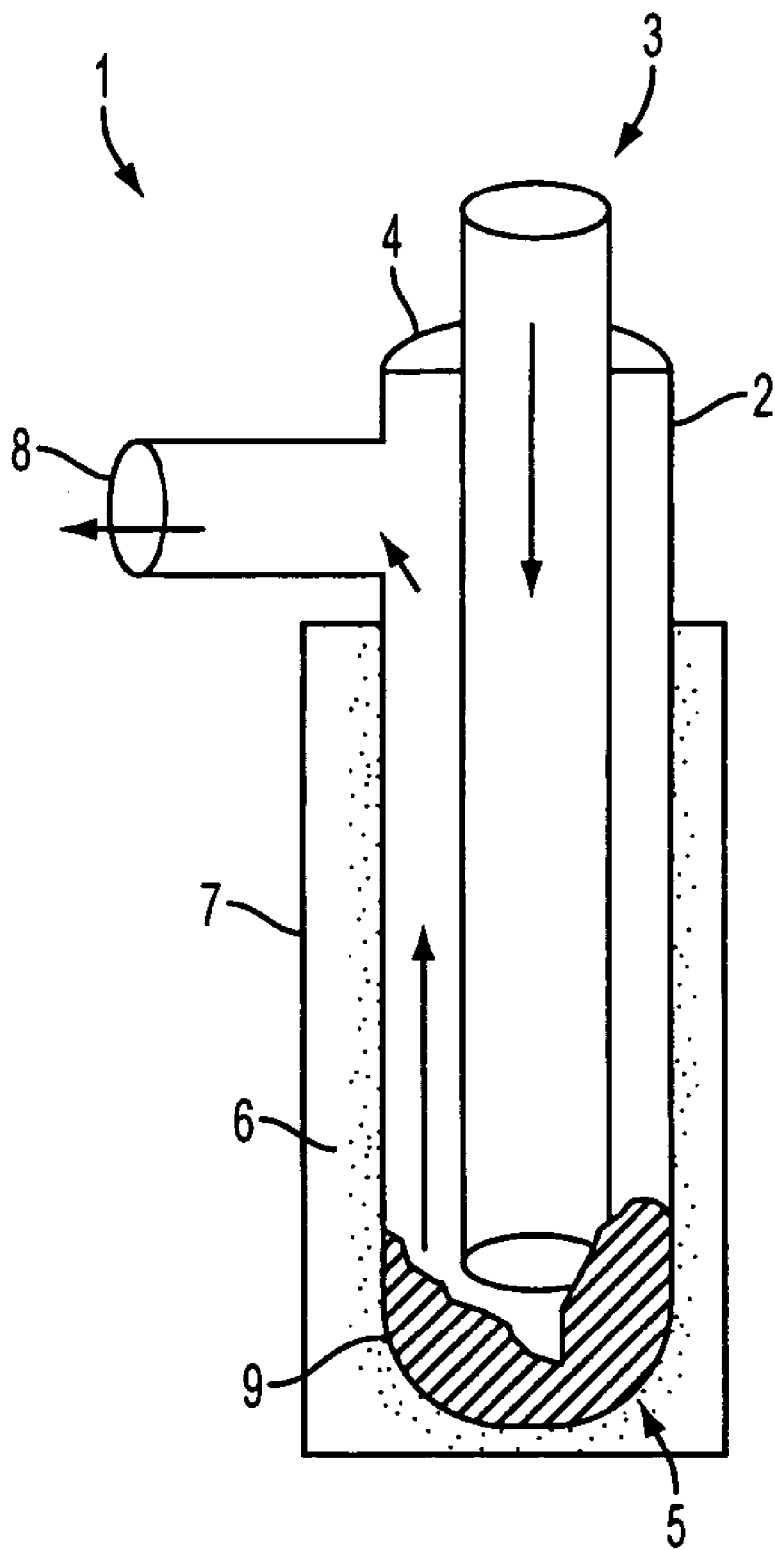
FIG. 1 is a cross-sectional diagram of an embodiment of a hyperpolarized $^{129}$Xe accumulator in the prior art.

FIG. 1 shows an embodiment of the apparatus in the prior art for freezing $^{129}$Xe to separate it from other gases in a gas mixture and to accumulate it. An accumulation cell 1 comprises two concentric cells, an outer cell 2 and an insulated inner cell 3. The accumulation cell 1 is placed in a cryogen 6, such as liquid nitrogen, contained in a dewar 7. The outer cell has a first end 4 and a second end 5. The cryogen temperature is below the freezing point of $^{129}$Xe but above the freezing point of the other components of the gas mixture. The outer cell 2 is in contact with the cryogen 6.

The gas mixture is flowed down the inner cell 3. The $^{129}$Xe freezes at the second end 5 of the outer cell 2 where it first contacts the cold surface of the outer cell 2 which is in contact with the cryogen 6. The other gases in the gas mixture are flowed up the outer cell 2 to the first end 4 of the outer cell and exhausted out of exhaust port 8.

As frozen $^{129}$Xe 9 is accumulated, the inner surface of second end 5 of the outer cell 2 becomes covered by frozen $^{129}$Xe 9. As more of the gas mixture is flowed through the inner cell 3, additional frozen $^{129}$Xe forms another layer on top of the existing frozen $^{129}$Xe 9 increasing the thickness of the frozen $^{129}$Xe 9. The volume of the lump of frozen $^{129}$Xe 9 that can be accumulated depends on the open volume of the second end 5 of the outer cell 2. If this region becomes full of frozen $^{129}$Xe 9, the flow of the gas mixture is stopped.

In addition, the frozen $^{129}$Xe 9 loses polarization faster if it is at a temperature just below its freezing point as compared to a lower temperature. Longer relaxation times are achieved, and longer accumulation times are permissible, if the frozen $^{129}$Xe 9 is maintained at temperatures well below its freezing point. In order for new gaseous $^{129}$Xe to freeze on the previously deposited $^{129}$Xe 9, heat must be transported through the previously deposited $^{129}$Xe 9, thereby warming it. The thermal conductivity of $^{129}$Xe is extremely poor. Therefore, the steady state temperature of the surface of the deposited $^{129}$Xe 9 will be in equilibrium at the freezing point of $^{129}$Xe and no lower. The relaxation of the polarized $^{129}$Xe is faster at this temperature than at any lower temperature.

Moreover, losses of polarization occur when the frozen $^{129}$Xe lingers at its freezing point, either during freezing or thawing. If the building up of frozen $^{129}$Xe during freezing becomes too thick, the accumulated frozen $^{129}$Xe 9 can insulate newly deposited $^{129}$Xe, slowing its cooling through its freezing point. In addition, warming the outer cell 2 to thaw a lump of frozen $^{129}$Xe 9 cannot be done rapidly, causing the frozen $^{129}$Xe 9 to dwell near its freezing point. Also, warming the outer cell 2 to thaw a thick lump of frozen $^{129}$Xe 9 can result in an insulating vapor barrier, which can further slow the thawing process.

The present invention, one preferred embodiment of which is shown in FIGS. 2a and 2B, comprises an accumulation cell 11 further comprising a heat exchanger tube 12 and a concentric inner tube 13. The heat exchanger tube 12 is placed in a cryogen 18, such as liquid nitrogen or other cryogen known to those skilled in the art contained in dewar 19. The cryogen is at a temperature that is below the freezing point of $^{129}$Xe but above the freezing points of the other gases in the gas mixture. The outer surface 17 of the heat exchanger tube 12 is in contact with the cryogen 18.

Reversing the flow of the gas mixture from the direction used in the prior art will cause the gas mixture to enter the first end 14 of the heat exchanger tube 12 and flow down the heat exchanger tube 12 to the second end 15. This change alone has two significant drawbacks. First the frozen $^{129}$Xe would accumulate just below the surface 20 of the cryogen. The thickness of the frozen $^{129}$Xe would increase eventually stopping the flow of the gas mixture. Second, if the level 20 of the cryogen drops, the frozen $^{129}$Xe deposited at the initial level of the cryogen will be exposed to higher temperatures, allowing it to thaw. Although, the now gaseous $^{129}$Xe will be picked up by the flowing gas mixture and carried by it to a new contact with frozen $^{129}$Xe, it will have incurred a freeze-thaw cycle, which can result in loss of polarization.

Therefore, the present invention involves both reversing the flow of the gas mixture, as described above, and controllably refrigerating the outer surface 17 of the heat exchanger tube 12, as described below. Controllably refrigerating the outer surface 17 the heat exchanger tube 12 involves controllably refrigerating additional adjacent area on the outer surface 17 of the heat exchanger tube 12 beginning with the second end 15. In the preferred embodiment shown in FIGS. 2A and 2B, this is accomplished by beginning with the cryogen level 20 shown in FIG. 2A. Then, as shown in FIG. 2B, the dewar 19 is controllably raised, thereby raising the cryogen level 20. This increases the area of the outer surface 17 of the heat exchanger tube 12 refrigerated. As frozen $^{129}$Xe 21 accumulates on inner surface 16 of the heat exchanger tube 12, the cryogen level 20 is raised to refrigerate additional adjacent areas on the outer surface 17 of the heat exchanger tube 12. As the cryogen level 20 is raised, the frozen $^{129}$Xe 21 deposits on new regions of the inner surface 16 of the heat exchanger tube 12 allowing a uniform thickness of frozen $^{129}$Xe 21 to deposit on the large areas of the inner surface 16 of the heat exchanger tube 12, as shown in FIG. 2B.

The present invention also comprises accumulating the frozen $^{129}$Xe in a relatively strong magnetic field, e.g., 500 Gauss or higher. The magnetic field can be provided by any one of a number of means known to those skilled in the art.

Tests of the present invention have been performed. A uniform accumulation time of ten minutes was used to minimize relaxation losses in the frozen state. $^{129}$Xe polarization was determined from measurements in an NMR using the known $^{129}$Xe concentration deduced from the gas mixture and pressure. After production was complete, the $^{129}$Xe was thawed. Gas polarization was determined again in the same NMR, this time using the $^{129}$Xe concentration determined by pressure only. Results are reported in the table below. Uncertainties are 5%. No correction was made for known losses due to the $^{129}$Xe being in a frozen state for ten minutes. The recovery ratio was indistinguishable from 100% for large quantity accumulations up to 0.5 liter, and only slightly lower for larger quantities, as shown below:

| Xenon Flow (liters/hour) | Frozen Volume (ml) | Production Polarization (%) | Thawed Xenon Polarization (%) | Recovery Ratio (%) |
|---|---|---|---|---|
| 0.6 | 100 | 47.4 | 47.3 | 99.8 |
| 3 | 500 | 24.5 | 24.4 | 99.6 |
| 4.5 | 750 | 19.1 | 17.6 | 92.0 |
| 6 | 1000 | 16.4 | 14.5 | 88.5 |

Referring to FIGS. 2A and 2B, controllably refrigerating the heat exchanger tube 12 can be accomplished by means other than controllably raising the level of the cryogen 20 by raising the dewar 19 to increase the area of the outer surface 17 of the heat exchanger tube 12 refrigerated. The heat exchanger tube 12 may be more fully immersed in the cryogen 18. Still another method would be to raise the level 20 of the cryogen in a motionless dewar 19 by adding additional cryogen 18 or displacing cryogen 18 either mechanically or with gas pressure on a separate part of the dewar 19. Still another method of controllably refrigerating the heat exchanger tube 12 would involve controllably exposing more of the outer surface 17 of the heat exchanger tube 12 to a mechanically refrigerated volume.

It is possible precisely to control the level 20 of the cryogen relative to the heat exchanger tube 12 by several methods, known to those skilled in the art. One preferred embodiment uses a level sensor in the cryogen and stepper motor and linear actuator mechanically to immerse the heat exchanger tube 12 in the cryogen 18 or to raise the dewar 19 holding the cryogen 18 relative to the heat exchanger tube 12.

In one preferred embodiment the relative motion of the heat exchanger tube 12 and dewar 19 was controlled initially at 1.2 cm/min, but changed to 1 cm/min during freezing of the $^{129}$Xe.

Figure 3A:
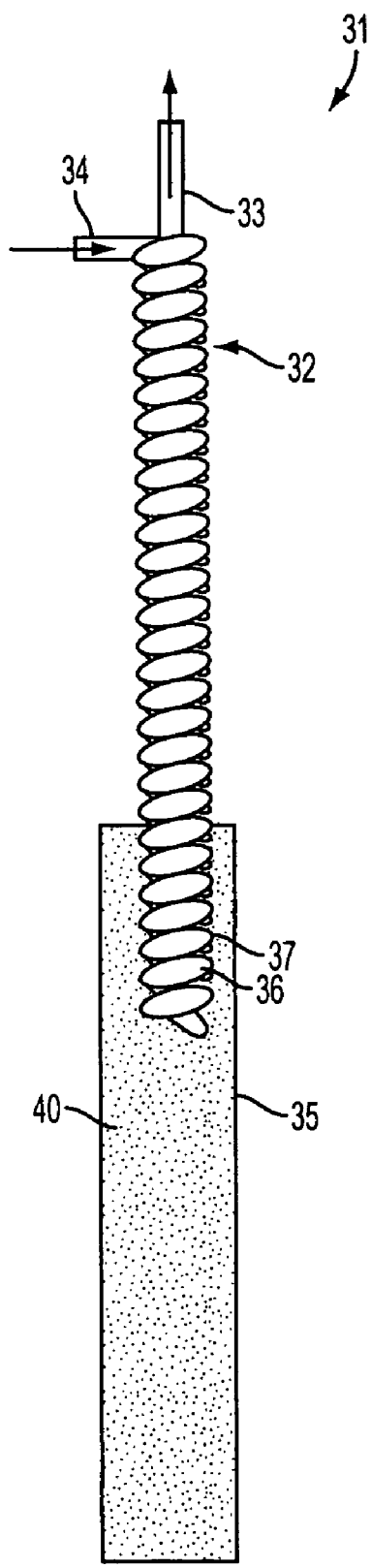
FIG. 3A is a cross-sectional diagram of another preferred embodiment of the present invention in which a heat exchanger tube is partially enclosed in a refrigerated volume.
Figure 3B:
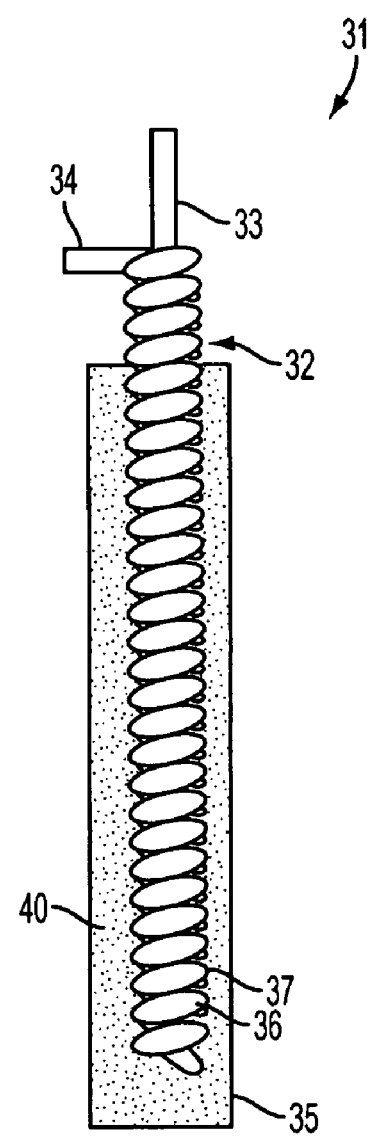
FIG. 3B is a cross-sectional diagram of another preferred embodiment of the present invention in which a heat exchanger tube is fully enclosed in a refrigerated volume.

Another preferred embodiment of the present invention is shown in FIGS. 3A and 3B. In this embodiment, the accumulation cell 31 comprises a heat exchanger tube 32 with a changed configuration. The present invention no longer requires the delivery of the gas mixture comprising $^{129}$Xe to a location well below the cryogen level. The heat exchanger tube 32 need not be a tube with a concentric inner tube to exhaust the unfrozen gases. An improved embodiment of the heat exchanger tube 32, as shown in FIGS. 3A and 3B, is a helical heat exchanger tube 32 wrapped around an inner tube 33. The heat exchanger tube has a first end 34 and a second end 35 and an inner surface 36 and an outer surface 37. The gas mixture enters the first end 34 of the heat exchanger tube 32 and flows down the heat exchanger tube 32 to the second end 35. The second end 35 of heat exchanger tube 32 is placed in a refrigerated volume 40. The helical geometry of the heat exchanger tube 32 provides substantially more outer surface 37 to be controllably refrigerated and substantially more inner surface 36 on which the frozen $^{129}$Xe can be deposited. The outer surface 37 of the heat exchanger tube 32 is then controllably refrigerated beginning with its second end 35 by controllably exposing additional adjacent area of the outer surface 37 of the heat exchanger tube 32 to the mechanically refrigerated volume as shown in FIG. 3B.

Figure 4:
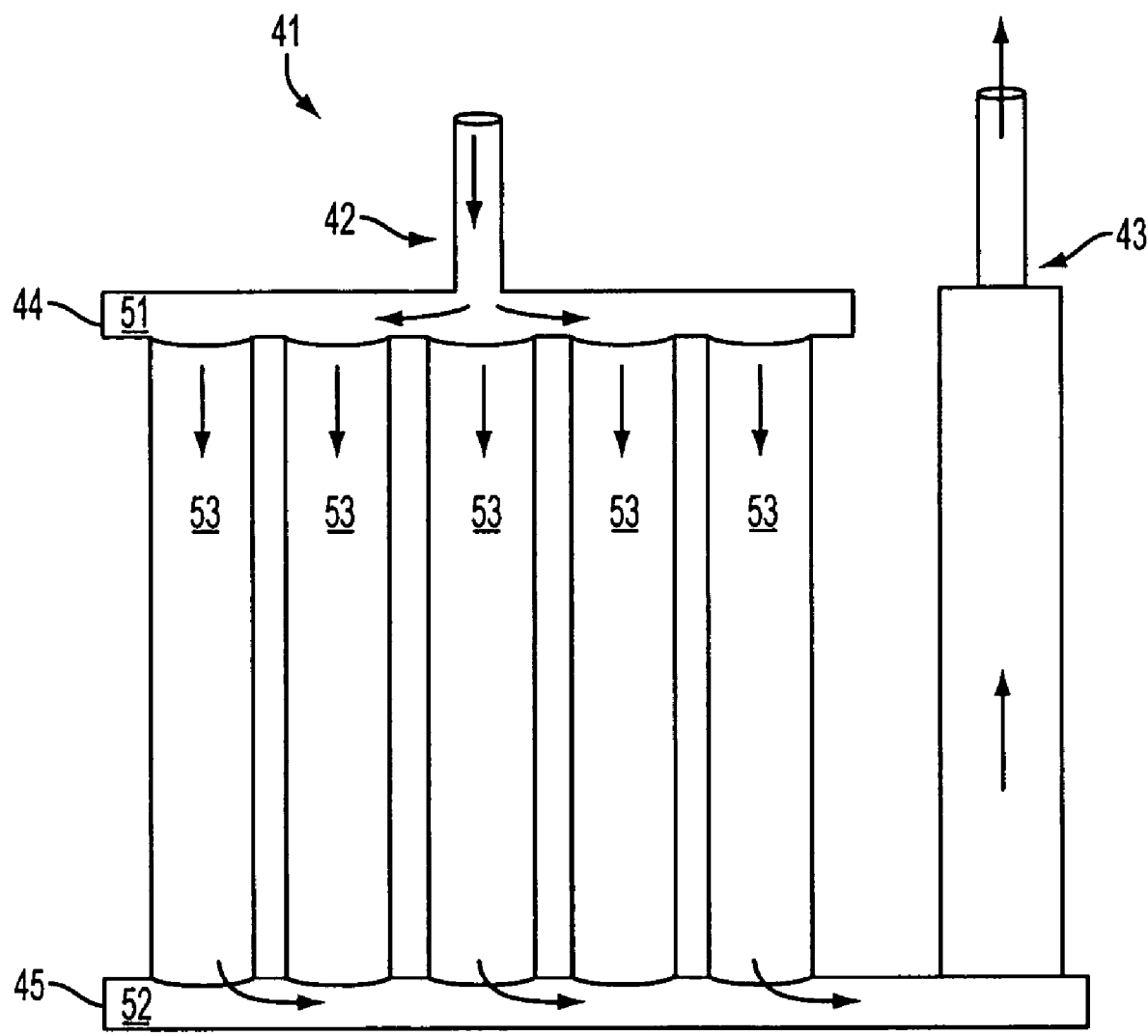
FIG. 4 is a cross-sectional diagram of a heat exchanger tube of another preferred embodiment of the present invention.

Another preferred embodiment of the present invention, as shown in FIG. 4, comprises a heat exchanger tube 42 of yet another geometry. This geometry can achieve a very high packing fraction, or surface to volume ratio. The accumulation cell 41 comprises a heat exchanger tube 42 of multiple tubes 53 and a separate tube 43. The heat exchanger tube has a first end 44 and a second end 45 and each multiple tube has an inner surface 46 and an outer surface 47. The gas mixture is flowed down the vertical tubes 53 of the heat exchanger tube 42 from the first end of the heat exchanger tube 44 to the second end 45 of the heat exchanger tube 42. The heat exchanger tube is then controllably refrigerated, beginning with the second end 45, as described above. The unfrozen gas is then exhausted through tube 43. This geometry has, however, proved challenging to fabricate. The attachment of multiple glass vertical tubes 53 at both ends to input 51 and output 52 manifolds results in thermal stresses and fractures when the molten glassware cools. Quartz has a very low index of thermal expansion and withstands these stresses, which are subsequently removed by annealing.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

The invention claimed is:

1. A method for accumulating hyperpolarized $^{129}$Xe comprising:
    adapting a heat exchanger tube with an inner surface and an outer surface and a first end and a second end to permit gas to flow therethrough from the first end to the second end;
    flowing a gas mixture comprising hyperpolarized $^{129}$Xe from the first end to the second end of the heat exchanger tube;
    applying a magnetic field to the heat exchanger tube; and
    controllably refrigerating the outer surface of the heat exchanger tube, by exposing a controllably larger area of the tube as freezing progresses beginning with the second end of the heat exchanger tube, to a temperature that is at least low enough to cause the $^{129}$Xe to freeze on the inner surface of the heat exchanger tube.

2. The method of claim 1 wherein the controllably refrigerating comprises:
    controllably contacting the outer surface of the heat exchanger tube with liquid nitrogen.

3. The method of claim 1 wherein the controllably refrigerating comprises controllably exposing the outer surface of the heat exchanger tube to a refrigerated volume.

4. The method of claim 1 wherein the temperature is that of liquid nitrogen.

5. An apparatus for accumulating hyperpolarized $^{129}$Xe comprising:
    a heat exchanger tube with an outer tube having an inner surface and an outer surface and an insulated inner tube, the outer tube having a first end and a second end for accumulating hyperpolarized $^{129}$Xe from a gas mixture flowing therethrough from the first end to the second end;
    a magnetization means to apply a magnetic field to the heat exchanger tube; and
    a refrigeration means for controllably refrigerating the outer surface of the heat exchanger tube, beginning with the second end, to a temperature that is at least low enough to cause the $^{129}$Xe to freeze on the inner surface of the heat exchanger tube.

6. The apparatus of claim 5 wherein the heat exchanger tube is helical in shape.

7. The apparatus of claim 5 wherein the heat exchanger tube comprises multiple tubes.

8. A method for accumulating hyperpolarized $^{129}$Xe comprising:
    adapting a heat exchanger tube with an inner surface and an outer surface and a first end and a second end to permit gas to flow therethrough from the first end to the second end;
    flowing a gas mixture comprising hyperpolarized $^{129}$Xe from the first end to the second end of the heat exchanger tube;
    applying a magnetic field to the heat exchanger tube; and
    controllably refrigerating the outer surface of the heat exchanger tube, beginning with the second end of the heat exchanger tube, to a temperature that is at least low enough to cause the $^{129}$Xe to freeze on the inner surface of the heat exchanger tube, wherein controllably refrigerating the outer surface comprises raising the level of the cryogen relative to the heat exchanger tube.

9. A method for accumulating hyperpolarized $^{129}$Xe comprising:

adapting a heat exchanger tube with an inner surface and an outer surface and a first end and a second end to permit gas to flow therethrough from the first end to the second end;

flowing a gas mixture comprising hyperpolarized $^{129}$Xe from the first end to the second end of the heat exchanger tube;

applying a magnetic field to the heat exchanger tube; and controllably refrigerating the outer surface of the heat exchanger tube, beginning with the second end of the heat exchanger tube, to a temperature that is at least low enough to cause the $^{129}$Xe to freeze on the inner surface of the heat exchanger tube, wherein the controllable refrigeration is raised such that a uniform thickness of frozen $^{129}$Xe is formed on the inner surface of the heat exchanger tube.

10. An apparatus of claim 6 wherein the helical tube is wrapped around the inner tube.

* * * * *